(12) United States Patent
Bamberg et al.

(10) Patent No.: US 7,169,810 B2
(45) Date of Patent: Jan. 30, 2007

(54) GUANIDINE AND AMIDINE ACID DERIVATIVES AND ANALOGS AND METHODS OF USING THE SAME

(75) Inventors: Krister Bamberg, Mölndal (SE); Lanna Li, Mölndal (SE)

(73) Assignee: AstraZeneca AB, Sodertalje (SE)

( * ) Notice: Subject to any disclaimer, the term of this patent is extended or adjusted under 35 U.S.C. 154(b) by 244 days.

(21) Appl. No.: 10/475,054

(22) PCT Filed: Apr. 18, 2002

(86) PCT No.: PCT/SE02/00770

§ 371 (c)(1),
(2), (4) Date: Oct. 17, 2003

(87) PCT Pub. No.: WO02/085844

PCT Pub. Date: Oct. 31, 2002

(65) Prior Publication Data

US 2004/0138300 A1     Jul. 15, 2004

(30) Foreign Application Priority Data

Apr. 20, 2001  (SE) .................................. 0101386

(51) Int. Cl.
*A01N 37/34* (2006.01)
*A61K 31/275* (2006.01)

(52) U.S. Cl. ...................... 514/522; 514/553; 514/567; 514/568; 558/414; 562/465

(58) Field of Classification Search ................ 514/522, 514/553, 567, 568; 558/414; 562/465
See application file for complete search history.

(56) References Cited

FOREIGN PATENT DOCUMENTS

| WO | WO 98/14192 | | 4/1998 |
|---|---|---|---|
| WO | WO-99/62870 A1 | | 12/1999 |
| WO | WO 99/62871 | * | 12/1999 |
| WO | WO-99/62871 A1 | | 12/1999 |
| WO | WO-99/62872 A1 | | 12/1999 |
| WO | WO 00/46215 | | 8/2000 |
| WO | WO 00/48603 | | 8/2000 |
| WO | WO-01/40172 A1 | | 6/2001 |

* cited by examiner

*Primary Examiner*—Thurman K. Page
*Assistant Examiner*—Chukwuma Nwaonicha
(74) *Attorney, Agent, or Firm*—Anita Skeppstedt; Cozen O'Connor, P.C.

(57) ABSTRACT

The present invention releates to certain novel guanidine or amidine acid derivatives and analogs, to a process for preparing such compounds, having the utility in clinical conditions associated with insulin resistance, to methods for their therapeutic use and to pharmaceutical compositions containing them.

11 Claims, No Drawings

GUANIDINE AND AMIDINE ACID DERIVATIVES AND ANALOGS AND METHODS OF USING THE SAME

RELATED APPLICATIONS

This application is a national stage filing under 35 U.S.C. 371 of International Application PCT/SE02/00770, filed Apr. 18, 2002, which claims priority from Sweden Application No. 0101386-1, filed Apr. 20, 2001, the specifications of each of which are incorporated by reference herein. International Application PCT/SE02/00770 was published under PCT Article 21(2) in English.

FIELD OF INVENTION

The present invention relates to certain novel guanidine or amidine acid derivatives and analogues, to a process for preparing such compounds, having the utility in clinical conditions associated with insulin resistance, to methods for their therapeutic use and to pharmaceutical compositions containing them.

BACKGROUND OF THE INVENTION

Insulin resistance, defined as reduced sensitivity to the actions of insulin in the whole body or individual tissues such as skeletal muscle, myocardium, fat and liver prevail in many individuals with or without diabetes mellitus. The insulin resistance syndrome, IRS, refers to a cluster of manifestations including insulin resistance with accompanying hyperinsulinemia, possibly type 2 diabetes mellitus, arterial hypertension, central (visceral) obesity, dyslipidemia observed as deranged lipoprotein levels typically characterised by elevated VLDL (very low density lipoproteins) and reduced HDL (high density lipoproteins) concentrations, the presence of small, dense LDL (Low Density Lipoprotein) particles and reduced fibrinolysis.

Recent epidemiological research has documented that individuals with insulin resistance run a greatly increased risk of cardiovascular morbidity and mortality, notably suffering from myocardial infarction and stroke. In non-insulin dependent diabetes mellitus these atherosclerosis related conditions cause up to 80% of all deaths.

In clinical medicine there is at present only limited awareness of the need to increase the insulin sensitivity in IRS and thus to correct the dyslipidemia which is considered to cause the accelerated progress of atherosclerosis.

Furthermore there is at present no pharmacotherapy available to adequately correct the metabolic disorders associated with IRS. To date, the treatment of type 2 diabetes mellitus has been focused on correction of the deranged control of carbohydrate metabolism associated with the disease. Stimulation of endogenous insulin secretion by means of secretagogues, like sulphonylureas, and if necessary administration of exogenous insulin are methods frequently used to normalise blood sugar but that will, if anything, further enhance insulin resistance and will not correct the other manifestations of IRS nor reduce cardiovascular morbidity and mortality. In addition such treatment involves a significant risk of hypoglycemia with associated complications.

Other therapeutic strategies have focused on aberrations in glucose metabolism or absorption, including biguanides, such as methformin, or glucosidase inhibitors, such as acarbose. Although these agents have been efficacious to a degree, their limited clinical effect is associated with side effects.

A novel therapeutic strategy involves the use of insulin sensitising agents, such as the thiazolidinediones which at least in part mediate their effects via an agonistic action on nuclear receptors. Ciglitazone is the prototype in this class. In animal models of IRS these compounds seem to correct insulin resistance and the associated hypertriglyceridaemia and hyperinsulinemia, as well as hyperglycaemia in diabetes, by improving insulin sensitivity via an effect on lipid transport and handling primarily in adipocytes, leading to enhanced insulin action in skeletal muscle, liver and adipose tissue.

Ciglitazone as well as later described thiazolidinediones in clinical development either have been discontinued reportedly due to unacceptable toxicity or show inadequate potency. Therefore there is a need for new and better compounds with insulin sensitizing properties.

DESCRIPTION OF THE INVENTION

The invention relates to compounds of the general formula (I)

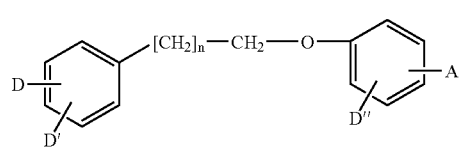

and stereo and optical isomers and racemates thereof as well as pharmaceutically acceptable salts, solvates, prodrugs, tautomers, and crystalline forms thereof, in which formula A is situated in the ortho, meta or para position (preferably in the meta or para position, ideally in the para position) and represents

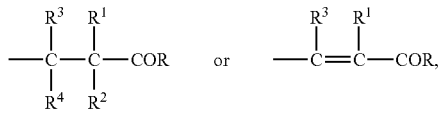

wherein
R is hydrogen;
— $OR^a$, wherein $R^a$ represents hydrogen, alkyl, aryl or alkylaryl;
— $NR^aR^b$, wherein $R^a$ and $R^b$ are the same or different and $R^a$ is as defined above and $R^b$ represents hydrogen, alkyl, aryl, alkylaryl, cyano, —OH, —Oalkyl, —Oaryl, —Oalkylaryl, —$COR^c$ or —$SO_2R^d$, wherein $R^c$ represents hydrogen, alkyl, aryl or alkylaryl and $R^d$ represents alkyl, aryl or alkylaryl;
$R^1$ is alkyl, aryl, alkene, alkyne, cyano;
— $OR^e$, wherein $R^e$ is alkyl, acyl, aryl or alkylaryl;
— $O$—$[CH_2]_m$—$OR^f$, wherein $R^f$ represents hydrogen, alkyl, acyl, aryl or alkylaryl and m represents an integer 1–8;
— $OCONR^aR^c$, wherein $R^a$ and $R^c$ are as defined above;
— $SR^d$, wherein $R^d$ is as defined above;
— $SO_2NR^aR^f$, wherein $R^f$ and $R^a$ are as defined above;
— $SO_2OR^d$, wherein $R^d$ is as defined above;
— $COOR^d$, wherein $R^d$ is as defined above;
$R^2$ is hydrogen, halogen (preferably fluorine), alkyl, aryl, or alkylaryl, $R^3$ and $R^4$ are the same or different and each represents hydrogen, alkyl, aryl, or alkylaryl, n is an integer 1–6, D is situated in the ortho, meta or para position (preferably in the meta or para position, ideally in the para position) and represents (U)(T)C(H)—NH—

U is selected from =$NR^f$ or $NR^aR^f$, wherein $R^a$ is as defined above and $R^f$ is as defined above and may additionally comprise —$COOR^d$, —CN, —OH, —$SO_2R^d$ and —$COR^a$, wherein $R^a$ and $R^d$ are as defined above;

T is a group defined in U (except when U is =$NR^f$ then T cannot be =$NR^f$) or is hydrogen, or a group selected from $R^1$, wherein $R^1$ is defined above;

D' is situated in the ortho, meta or para position (preferably the ortho or meta position) and represents hydrogen, alkyl, acyl, aryl, alkylaryl, halogen, —CN, —$NO_2$, —$NR^fR^b$, wherein $R^f$ and $R^b$ are as defined above;

—$OR^f$, wherein $R^f$ is as defined above;

—$OSO_2R^d$, wherein $R^d$ is as defined above;

D" is situated in the ortho, meta or para position (preferably the ortho or meta position) and represents hydrogen, alkyl, acyl, aryl, alkylaryl, halogen, —CN, —$NO_2$, —$NR^fR^b$ wherein $R^f$ and $R^b$ are as defined above;

—$OR^f$, wherein $R^f$ is as defined above;

—$OSO_2R^d$, wherein $R^d$ is as defined above.

For ease of reference the definitions of formula I above is henceforth referred to as defined in Category A. Unless otherwise stated the definitions of the various substituents are as defined under Category A throughout the present application.

The compounds of the formula I are surprisingly effective in conditions associated with insulin resistance.

Category A2: preferred compounds of the present invention are those of formula I, wherein A is situated in the meta or para position and represents,

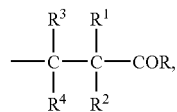

wherein

R is hydrogen;

—$OR^a$, wherein $R^a$ is as defined in Category A;

—$NR^aR^b$, wherein $R^a$ and $R^b$ are the same or different and $R^a$ is as defined in Category A and $R^b$ represents hydrogen, alkyl, aryl, alkylaryl, cyano, —OH, —Oalkyl or —Oalkylaryl;

$R^1$ is cyano;

—$OR^d$, wherein $R^d$ is as defined in Category A;

—O—$[CH_2]_m$—$OR^a$, wherein m and $R^a$ are as defined in Category A;

$R^2$ is hydrogen or alkyl;

$R^3$ is hydrogen or alkyl;

$R^4$ is hydrogen;

n is an integer 2–4;

D is situated in the ortho, meta or para position and represents

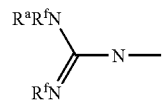

wherein $R^a$ is as defined above and $R^f$ is as defined above in category A and may additionally comprise —$COOR^d$, —CN, —OH—, —$SO_2R^d$ and —$COR^a$, wherein $R^a$ and $R^d$ are as defined above;

D' is situated in the ortho, meta or para position and represents hydrogen, alkyl, alkylaryl, halogen, —CN or —$NO_2$; —$OR^h$, wherein $R^h$ is hydrogen or alkyl;

D" is situated in the ortho, meta or para position and represents hydrogen, alkyl, alkylaryl, halogen, —CN or —$NO_2$; —$OR^h$, wherein $R^h$ is as defined above.

Category A3: further preferred compounds of the present invention are those within Category A2, wherein A is situated in the meta or para position;

R is —$OR^a$, wherein $R^a$ is hydrogen, alkyl or alkylaryl;

—$NHR^b$, wherein $R^h$ is hydrogen, alkyl, alkylaryl, cyano, —Oalkyl or —Oalkylaryl;

$R^1$ is —Oalkyl;

$R^2$ is hydrogen or alkyl;

$R^3$ is hydrogen or alkyl;

$R^4$ is hydrogen;

n is an integer 2–4,

D is situated in the para position and represents

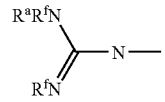

wherein $R^a$ and $R^f$ are as defined in Category A2;

D' is hydrogen.

D" is hydrogen.

Category A4: further preferred compounds of the present invention are those within Category A3, wherein A is situated in the para position;

R is —OH, —Oalkyl or —Oalkylaryl;

—$NH_2$, —NHOalkylaryl or —NHCN;

$R^1$ is —Oalkyl, preferably —Olower alkyl;

$R^2$ is hydrogen;

$R^3$ is hydrogen;

n is the integer 2 to 3;

D is situated in the para position, and represents,

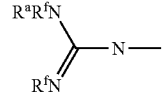

wherein $R^a$ is as defined in Category A and $R^f$ represents hydrogen, alkyl, aryl or —$COOR^d$, wherein $R^a$ is as defined in category A.

Category A5: further preferred compounds of the present invention are those within Category A4, wherein D represents

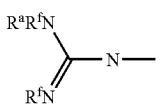

wherein $R^a$ is alkyl or aryl.

Category A6: further preferred compounds of the present invention are those within Category A5 wherein
R is —OH, —Oalkyl or —Oalkylaryl;

Category A7: further preferred compounds of the present invention are those within Category A6 wherein D represents

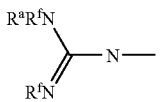

wherein $R^a$ represents alkyl or aryl and $R^f$ represents hydrogen, alkyl, aryl or —COOR$^d$, wherein $R^d$ is as defined in category A.

Category A8: further preferred compounds of the present invention are those within Category A7, wherein D represents

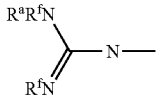

wherein $R^a$ is as defined in Category 7 and $R^f$ represents hydrogen, alkyl, aryl or —COOR$^d$, wherein $R^d$ represents alkyl or aryl.

Category A9: further preferred compounds of the invention are selected from Examples 1, 2, 3 and 4.

Category A10: further preferred compounds of the present invention are compounds which are one of the possible enantiomers.

In vivo hydrolysable esters of the compounds of Formula I are just one type of prodrug of the parent molecule. Other prodrugs of the parent molecule are envisaged such as amide prodrugs, and can be prepared by routine methodology well within the capabilities of someone skilled in the art. Prodrugs of the compound of Formula I are within the scope of the invention. Various prodrugs are known in the art. For examples of such prodrug derivatives, see:
a) Design of Prodrugs, edited by H. Bundgaard, (Elsevier, 1985) and Methods in Enzymology. 42: 309–396, edited by K. Widder, et al. (Academic Press, 1985);
b) A Textbook of Drug Design and Development, edited by Krogsgaard-Larsen and H. Bundgaard, Chapter 5 "Design and Application of Prodrugs", by H. Bundgaard p.113–191 (1991);
c) H. Bundgaard, Advanced Drug Delivery Reviews, 8:1–38 (1992);
d) H. Bundgaard, et al., Journal of Pharmaceutical Sciences, 77:285 (1988); and
e) N. Kakeya, et al., Chem Pharm Bull, 32:692 (1984).

The preferred examples of prodrugs include in vivo hydrolysable esters of a compound of the Formula I. Suitable pharmaceutically-acceptable esters for carboxy include $C_{1-8}$alkyl esters, $C_{5-8}$cycloalkyl esters, cyclic amine esters, $C_{1-6}$alkoxymethyl esters for example methoxymethyl, $C_{1-6}$alkanoyloxymethyl esters for example pivaloyloxymethyl, phthalidyl esters, $C_{3-8}$cycloalkoxycarbonyloxy$C_{1-6}$alkyl esters for example 1-cyclohexylcarbonyloxyethyl; 1,3-dioxolen-2-onylmethyl esters for example 5-methyl-1,3-dioxolen-2-onylmethyl; and $C_{1-6}$alkoxycarbonyloxyethyl esters for example 1-methoxycarbonyloxyethyl wherein alkyl, cycloalkyl and cyclicamino groups are optionally substituted by, for example, phenyl, heterocyclcyl, alkyl, amino, alkylamino, dialkylamino, hydroxy, alkoxy, aryloxy or benzyloxy, and may be formed at any carboxy group in the compounds of this invention.

It will also be understood that certain compounds of the present invention may exist in solvated, for example hydrated, as well as unsolvated forms. It is to be understood that the present invention encompasses all such solvated forms.

Throughout the specification and the appended claims, a given chemical formula or name shall encompass all stereo and optical isomers and racemates thereof, as well as mixtures in different proportions of the separate enantiomers, where such isomers and enantiomers exist, as well as pharmaceutically acceptable salts thereof and solvates thereof such as for instance hydrates. Isomers may be separated using conventional techniques, e.g. chromatography or fractional crystallisation. The enantiomers may be isolated by separation of racemate for example by fractional crystallisation, resolution or HPLC. The diastereomers may be isolated by separation of isomer mixtures for instance by fractional crystallisation, HPLC or flash chromatography. Alternatively the stereoisomers may be made by chiral synthesis from chiral starting materials under conditions which will not cause racemisation or epimerisation, or by derivatisation, with a chiral reagent. All stereoisomers are included within the scope of the invention.

The following definitions shall apply throughout the specification and the appended claims.

Unless otherwise stated or indicated, the term "alkyl" denotes a straight or branched, substituted or unsubstituted alkyl group having from 1 to 6 carbon atoms or a cyclic alkyl having from 3 to 6 carbon atoms. Preferably the term "alkyl" denotes a straight or branched, substituted or unsubstituted alkyl group having from 1 to 3 carbon atoms or a cyclic alkyl having 3 carbon atoms. Examples of said alkyl are methyl, ethyl, n-propyl, isopropyl, n-butyl, iso-butyl, sec-butyl, t-butyl and straight- and branched-chain pentyl and hexyl as well as cyclopropyl, cyclobutyl, cyclopentyl and cyclohexyl.

Unless otherwise stated or indicated, the term "alkoxy" denotes a group O-alkyl, wherein alkyl is as defined above.

Unless otherwise stated or indicated, the term "halogen" shall mean fluorine, chlorine, bromine or iodine, preferably fluorine.

Unless otherwise stated or indicated, the term "aryl" denotes a substituted or unsubstituted phenyl, furyl, thienyl or pyridyl group, or a fused ring system of any of these groups, such as naphthyl. Preferably "aryl" is a phenyl or naphthyl group.

Unless otherwise stated or indicated, the term "substituted" denotes an alkyl or an aryl group as defined above which is substituted by one or more alkyl, alkoxy, halogen, amino, thiol, nitro, hydroxy, acyl, aryl or cyano groups.

Unless otherwise stated or indicated, the term "alkylaryl" denotes a

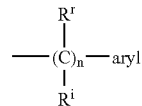

wherein n is an integer 1 to 6 and $R^r$ and $R^i$ are the same or different and each represents hydrogen or an alkyl or aryl group as defined above.

Unless otherwise stated or indicated, the term "acyl" denotes a group

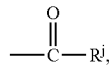

wherein $R^j$ is hydrogen, alkyl, alkoxy, aryl and alkylaryl as defined above.

Unless otherwise stated or indicated, the terms "alkenyl" and "alkynyl" denote a straight or branched, substituted or unsubstituted unsaturated hydrocarbon group having one or more double or triple bonds and having a maximum of 6 carbon atoms, preferably 3 carbon atoms.

Unless otherwise stated or indicated the term "protective group" ($R^p$) denotes a protecting group as described in the standard text "Protecting groups in Organic Synthesis", 2nd Edition (1991) by Greene and Wuts. The protective group may also be a polymer resin such as Wang resin or 2-chlorotrityl chloride resin.

Specific compounds of formula I include:

3-{4-[(4-{[anilino(methylimino)methyl]amino}phenethyl)oxy]phenyl}-2-ethoxypropanoic acid;

3-{4-[(4-{[anilino(phenylimino)methyl]amino}phenethyl)oxy]phenyl}-2-ethoxypropanoic acid;

3-(4-{[4-({[(tert-butoxycarbonyl)amino][(tert-butoxycarbonyl)imino]methyl}amino)-phenethyl]oxy}phenyl)-2-ethoxypropanoic acid;

3-(4-{[4-({[(tert-butoxycarbonyl)amino][(tert-butoxycarbonyl)imino]methyl}amino)-phenethyl]oxy}phenyl)-2(S)-ethoxypropanoic acid;

(2S)-3-(4-{4-[4-({[(tert-butoxycarbonyl)amino][(tert-butoxycarbonyl)imino]methyl}-amino)phenyl]butoxy}phenyl)-2-ethoxypropanoic acid; and (2S)-3-(4-{3-[4-({[(tert-Butoxycarbonyl)amino][(tert-butoxycarbonyl)imino]methyl}amino)phenyl]propoxy}phenyl)-2-ethoxypropanoic acid; and pharmaceutically acceptable salts thereof.

Methods of Preparation

The compounds of the invention may be prepared as outlined below according to any of methods A–J. However, the invention is not limited to these methods, the compounds may also be prepared as described for structurally related compounds in the prior art.

A. The compounds of formula I wherein $R^2$ and $R^4$ are hydrogen can be prepared by a condensation reaction, such as a Knoevenagel or Wittig type reaction, of a carbonyl compound of the formula II

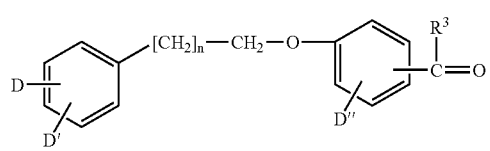

with a compound of the formula III or IV

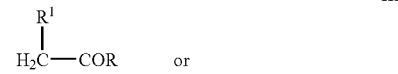

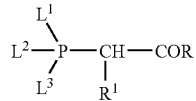

in which formulas D, D', D", n, R, $R^1$ and $R^3$ are as defined in Category A and $L^1=L^2=L^3$ are phenyl or $L^1=L^2$ are $OR^d$ (wherein $R^d$ is as defined in Category A) and $L^3$ is =O, and if desired, followed by reduction of the obtained double bond and removal of protective groups.

A1. In the condensation step approximately equimolar amounts of reactants are mixed in the presence of a base, such as sodium acetate, piperidine acetate, LDA or potassium tert-butoxide to provide the compound of formula I wherein A is the unsaturated moiety. This step may be carried out in the presence of an inert solvent or in the absence of solvent in which case the temperature should be sufficiently high to cause at least partial melting of the reaction mixture, a preferred such temperature is in the range of 100° C. to 250° C.

Sometimes it is necessary to add a dehydrating agent such as p-toluenesulfonic acid in order to achieve the formation of the double bond.

In a typical such reaction the aldehyde or ketone starting material and the compound of formula III are combined in approximately equimolar amounts and molar excess, preferably 1–5 fold, of anhydrous sodium acetate and the mixture is heated until it melts if necessary under vacuum. The compound of formula I wherein A is the unsaturated moiety, can then be isolated by mixing with water and acetone, followed by filtration of the formed precipitate. The crude product can be purified if desired, e.g. by recrystallization or by standard chromatographic methods.

This reaction can also be performed conveniently in a solvent such as toluene in the presence of piperidine acetate. The reaction mixture is refluxed in a Dean-Stark apparatus to remove water. The solution is then cooled and the olefin product isolated and purified, by standard methods.

The reaction can also be performed by mixing the aldehyde or ketone and the compound of formula III in dry tetrahydrofuran, slowly adding potassium tert-butoxide at −20° C. and quenching the reaction with acetic acid. The crude product is isolated and then dissolved in toluene and refluxed with p-toluenesulfonic acid in an Dean-Stark apparatus to remove the water. The product is then isolated and purified, by standard methods.

A2. The reaction can also be performed in the presence of titanium (IV) chloride and pyridine in an inert solvent, such as chloroform.

A3. The condensation step could also be performed as a Wittig-type reaction (cf. Comprehensive Organic Synthesis vol. 1 p. 755–781 Pergamon Press) or as described in the experimental part.

Approximately equimolar amounts of reactants II and IV, are mixed in the presence of a base such as tetramethylguanidine or potassium carbonate in a 1–5 fold molar excess. This reaction may be carried out in the presence of an inert solvent such as dichloromethane or isopropanol at a suitable temperature (−10° C. −+60° C.) and at a time long enough.

The compound of the formula II is prepared by coupling a compound of the formula V

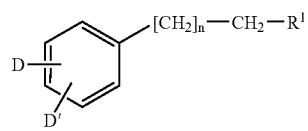

V with a compound of the formula VI

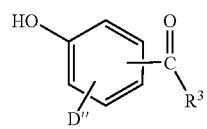

VI in which formulas D, D', D", n and $R^3$ are as defined in Category A (except D" should not be —$NR'R^b$) at, for example alkylation conditions or by a Mitsunobu reaction (Tsunoda, Tetr. Lett. 34, 1639–42 (1993), when necessary followed by modifications of the D-groups and removal of protective groups.

The group $R^1$ can be —OH or a leaving group, such as halogen, sulfonate or triflate.

The alkylation reaction and the Mitsunobu reaction can be carried out as described below.

The compounds of formula III, IV, V or VI are either commercially available or can be prepared by standard procedures known to anyone skilled in the art from commercially available starting materials.

The reduction of the olefin may be carried out by using a wide variety of reducing methods known to reduce carbon-carbon double bonds, such as catalytic hydrogenation in the presence of an appropriate catalyst, magnesium or sodium amalgam in a lower alcohol such as methanol, or hydrogen transfer reagents such as diethyl-2,5-dimethyl-1,4-dihydro-pyridine-3,5-dicarboxylate.

The catalytic hydrogenation can be conducted in alcohol, cellosolves, protic polar organic solvents, ethers, lower alifatic acids, and particularly in methanol, ethanol, methoxyethanol, dimethylformamide, tetrahydrofuran, dioxane, dimetoxyethane, ethyl acetate or acetic acid, either used alone or in mixture. Examples of the catalyst used include palladium black, palladium on activated charcoal, platinum oxide or Wilkinson's catalyst. The reaction can proceed at different temperatures and pressures depending on the reactivity of the aimed reaction.

In case of hydrogen transfer reaction with diethyl-2,5-dimethyl-1,4-dihydropyridine-3,5-dicarboxylate, equimolar amounts of reactants are mixed and the mixture is warmed to melting (140° C.–250° C.) under inert atmosphere or under vacuum.

B. The compounds of formula I where A=—$CR^3R^4$—$CR^1R^2$—COR, wherein $R^4$ is hydrogen can be prepared by reacting a carbonyl compound of formula II

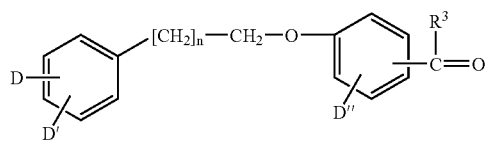

II with a compound of formula VII

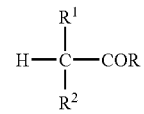

VII in which formulas D, D', D", n, $R^1$ and $R^3$ are as defined in Category A and $R^2$ is alkyl, aryl or alkylaryl, followed by dehydroxylation and if necessary by removal of protective groups.

In the reaction the compound of formula II is reacted with a compound of formula VII in the presence of a strong base such as LDA in an inert solvent followed by addition of a dehydroxylating agent such as borontrifluoride etherate.

The reaction can be carried out as described in the experimental section or by standard methods know to anyone skilled in the art.

The compound of formula VII are either commercially available or can be prepared by standard procedures.

C. The compounds of formula I where A=$CR^3R^4$—$CR^1R^2$—COR, can be prepared by an alkylation reaction with a compound of formula VIII

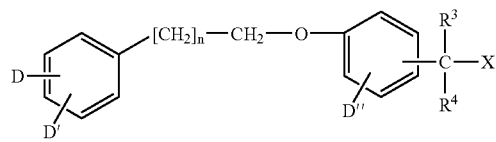

VIII where in X is a leaving group, such as halogen, sulfonates or triflates, on a compound of formula VII,

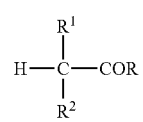

VII in which formulas D, D', D", n, R, $R^1$, $R^2$, $R^3$ and $R^4$ are as defined in Category A and, if desired, followed by removal of protective groups.

In the alkylation step the compound of formula VII is reacted with a compound of formula VIII in the presence of one or more bases such as potassium carbonate, triethylbenzylammonium chloride, sodium hydride, LDA, butyllithium or LHMDS and in a inert solvent such as acetonitrile, DMF or dichloromethane at a suitable temperature and time. The reaction can be carried out as described in the examples or by standard methods known in the literature. (Synth. Comm. 19(788) 1167–1175 (1989)).

The compound of formula VIII can be prepared from an alcohol of formula IX,

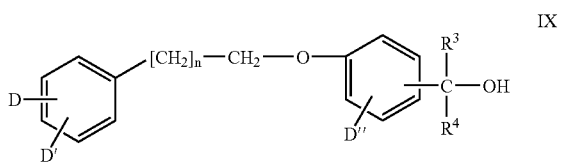

IX wherein D, D', D", n, R$^3$ and R$^4$ are as defined in Category A using standard methods or as described in the experimental section.

The compound of formula IX can be prepared from a compound of formula II either by reduction with a reducing agent known to convert a carbonyl group to a hydroxyl group such as lithium borohydride or sodium borohydride or by reaction with an organometallic compound such as an organolithium or a Grignard reagent by standard methods or as described in the experimental section.

D. The compounds of the invention of formula I can be prepared by reaction of a compound of the formula

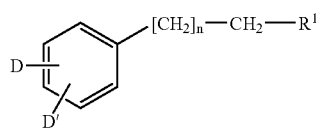

V with a compound of the formula X

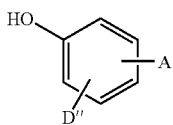

X in which formulas D, D', D", n and A are as defined in Category A, and R$^1$ is —OH or a leaving group such as halogen, sulfonate, triflate, either by an alkylation reaction or a Mitsunobu reaction, when nessecary followed by removal of protective groups.

The compound of formula X can be prepared in accordance to method A and in an analogous method to the preparation of the compound of formula VIII, as described above, from commercially available starting materials and compounds of formula III or IV.

D1. In an alkylation reaction the leaving group R$^1$ can be a sulfonate such as mesylate, nosylate, tosylate, or a halogen, such as bromine or iodine. The compounds of formula V and X, in approximately equimolar amounts or with an excess of one of the compounds, are heated to reflux temperature in an inert solvent, such as isopropanol or acetonitrile, in the presence of a base, such as potassium carbonate or cesium carbonate.

The mixture is refluxed for the necessary time, typically between 0.5 h to 24 h, the work up procedure usually include filtration, for removal of solid salt, evaporation and extraction with water and an organic solvent such as dichloromethane, ethyl acetate, or diethyl ether. The crude product is purified if desired e.g. by recrystallization or by standard chromatographic methods.

D2. The Mitsunobu reaction can be carried out according to standard methods.

In a typical Mitsunobu reaction a compound of formula V, wherein the group R$^1$ is a hydroxyl group, and a compound of formula X are mixed, in approximately equimolar amounts or with an excess of one of the compounds, in an inert solvent, such as chloroform, dichloromethane, or tetrahydrofuran. A slight molar excess of an azodicarboxylate, (1–4 equivalents) such as DEAD or ADDP and a phosphine (1–4 equivalents), such as tributylphosphine or triphenylphosphine are added and the reaction mixture is stirred at a temperature high enough, for example room temperature, and a time long enough (1–24 hours) to obtain the crude product, which can be worked up according to standard litterature methods and if desired purified, e.g. by standard chromatographic methods.

E. The compounds of formula I, wherein A is —CR$^3$R$^4$—CR$^1$R$^2$—COR, wherein R, R$^2$R$^3$ and R$^4$ are as defined in Category A and R$^1$ is
—OR$^e$, wherein R$^e$ is as defined in Category A,
—O—[CH$_2$]$_m$—OR$^f$, wherein m and R$^c$ are as defined in Category A,
—OCONR$^a$R$^c$, wherein R$^a$ and R$^c$ are as defined in Category A,
can be prepared by converting a compound of formula XI

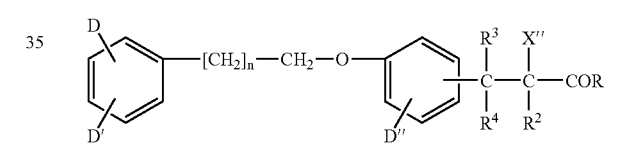

XI wherein D, D', D", n, R, R$^2$, R$^3$ and R$^4$ are as defined in Category A and X" is —OH followed, if necessary, by removal of protective groups.

The reaction may be carried out as an alkylating reaction, a Mitsunobu reaction, an esterfication reaction or by reaction with isocyanates. The alkylating reaction may be carried out using a variety of alkylating agents, such as alkyl halide. The esterfication reaction may be carried out using a variety of acylating agents such as Cl—CO—R$_d$ (wherein R$^d$ is as defined in Category A) and the Mitsunobu reaction may be carried out using an alcohol such as phenol.

The reactions can be carried out in accordance with methods known to those skilled in the art or as described in the examples.

The compound of formula XI can be prepared by reaction of a compound of formula V

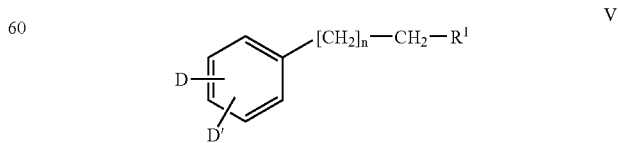

V with a compound of formula XII

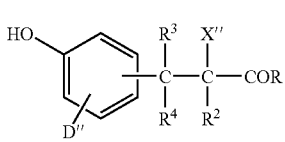

XII

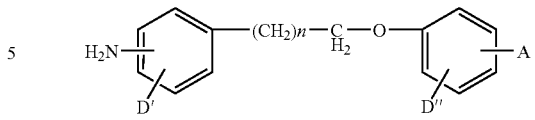

XVI wherein D, D', D", n, R, R², R³, R⁴ are as defined in Category A and R¹ is —OH or a leaving group such as halogen, sulfonate or triflate and X" is —OH followed, if necessary, by removal of protective groups.

The reaction can be performed as described above or by standard methods know to anyone skilled in the art.

The compound of formula XII can be prepared according to literature methods from commercially available starting materials.

F. The compounds of formula I wherein A is —CR³R⁴—CR¹ R² —COR, and R, R², R³ and R⁴ are as defined in Category A and R¹ is —SR$^d$, wherein R$^d$ is as defined in Category A, can be prepared by reacting a compound of the formula XIII

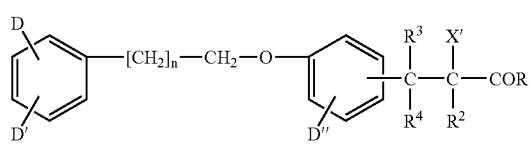

XIII wherein D, D', D", n, R, R², R³, R⁴ are as defined in Category A and X' is halogen, a thiol in a substitution reaction. The reaction can be carried out in accordance to methods known to those skilled in the art or as described in the examples.

The compound of formula XIII can be prepared in accordance to method D from either commercially available starting materials or from starting materials prepared by standard procedures from commercially available starting materials.

G. The compounds of formula I where R is —OH can be prepared from a compound of formula I where in R is —OR$^p$, wherein R$^p$ is a protective group such as alkyl, aryl, alkylaryl or a polymer resin such as Wang resin or 2-chlorotrityl chloride resin, by removal of the protective group by hydrolysis. The hydrolysis can be performed according to standard methods either under basic or acidic conditions.

H. The compound of formula I wherein R is —NR$^a$R$^b$ can be prepared by reacting a compound of formula I when R is —OH with a compound of formula HNR$^a$R$^b$ in the presence of a peptide coupling system (e.g. EDC, DCC, HBTU, TBTU or PyBop or oxalylchloride in DMF), an appropriate base (e.g. pyridine, DMAP, TEA or DiPEA) and a suitable organic solvent (e.g. dichloromethane, acetonitrile or DMF) in accordance to methods known to those skilled in the art or as described in the examples.

I. The compound of formula I where S is =NR$^f$ and T is —NR$^a$R$^f$ can be prepared by reacting a compound of formula XVI with a guanylating reagent according to the known methods in the literature(Alan R. Katritzky et al., Comprehensive Organic Functional Group Transformation, Vol.6, p.640-), and as described in the examples. The reagent can be used as ready-made or generated in situ.

The reaction can involve the use of an amidine or an amidinium salt (known as the Rathke procedure), such as an S-alkylisothiouronium salt, or an O-alkylisouronium salt, or an O-phosphorylisouronium salt, or a chloformamidinium salt (Vilsmeier salt). It can also be an aminoiminomethane sulfonic acid (N-substituted or unsubstituted). Other type of carboxamidines, such as 3,5-dimethyl-1-H-pyrazole-1-carboxamidine (nitrate) 1H-pyrazole-1-carboxamidine (hydrochloride), or a N, N'-bisurethane-carboxamidine (for example N N'-di-boc-N'-triflylguanidine, N, N'-di-Cbz—N'-triflylguanide, (J. Org Chem. 1998, 3804)) can also be used in this synthesis.

The reaction can involve the use of a urea derivative (thiourea derivative) together with a base (for example Et₃N, 2-chloro-1-methylpyridinium iodide) and/or a metal catalyst (for example AgNO₃, HgCl₂).

The reaction can involve the use of a cyanamide and an amine, or a dihalide and an amine, or a carbodiimide.

J. The compound of formula I where S is =NR$^F$ and T is —NR$^a$R$^f$ can be prepared by transforming a compound of formula XVI to its unsubstituted amidine or guanidine (for example by reacting with N N'-di-boc-N'-triflylguanidine or N, N'-di-Cbz-N'-triflylguanide, followed by deprotecting), followed by alkylation, acylation, and reacting with a sulfonylchloride and other known methods in the literature to the substituted derivatives.

The compound of formula I where S is =NR$^f$ and T is —NR$^a$R$^f$ can be prepared by transforming a compound of formula XVI to its isothiourea derivatives, or thiourea derivative, or urea derivatives, or cyanamide derivative, or carbodiimide derivatives which then can be reacted further using the methods described above.

K. The compound of formula I where S is =NR$^f$ and T is —H can be prepared by reacting a compound of formula XVI with a suitable reagent according to the known methods in the literature (Alan R. Katritzky et al., Comprehensive Organic Functional Group Transformation, Vol. 5, p.742-). The reaction can involve the use of an ortho-ester, or an acetal or a thioester. The reaction can involve the use of a formamide or a thioformamide with a chlorinating agent, such as PCl₅ or an activating agent such as dimethyl sulfate.

The compounds of the invention may be isolated from their reaction mixtures using conventional techniques.

Persons skilled in the art will appreciate that, in order to obtain compounds of the invention in an alternative and in some occasions, more convenient manner, the individual process steps mentioned hereinbefore may be performed in different order, and/or the individual reactions may be performed at different stage in the overall route (i.e. chemical transformations may be performed upon different intermediates to those associated hereinbefore with a particular reaction).

In any of the preceeding methods of preparation A-K, where necessary, hydroxy, amino or other reactive groups may be protected using a protecting group, as described in the standard text "Protective groups in Organic Synthesis", 2$^{nd}$ Edition (1991) by Greene and Wuts. The protecting group may also be a resin, such as Wang resin or 2-chlorotrityl chloride resin. The protection and deprotection of functional groups may take place before or after any of the reaction steps described hereinbefore. Protecting groups may be removed in accordance to techniques which are well known to those skilled in the art.

The expression "inert solvent" refers to a solvent which does not react with the starting materials, reagents, intermediates or products in a manner which adversely affects the yield of the desired product.

Pharmaceutical Preparations

The compounds of the invention will normally be administered via the oral, parenteral, intravenous, intramuscular, subcutaneous or in other injectable ways, buccal, rectal, vaginal, transdermal and/or nasal route and/or via inhalation, in the form of pharmaceutical preparations comprising the active ingredient either as a free acid, or a pharmaceutical acceptable organic or inorganic base addition salt, in a pharmaceutically acceptable dosage form. Depending upon the disorder and patient to be treated and the route of administration, the compositions may be administered at varying doses.

The compounds of the invention may also be combined with other therapeutic agents which are useful in the treatment of disorders associated with the development and progress of atherosclerosis such as hypertension, hyperlipidemias, dyslipidemias, diabetes and obesity.

Suitable daily doses of the compounds of the invention in therapeutical treatment of humans are about 0.0001–100 mg/kg body weight, preferably 0.001–10 mg/kg body weight.

According to a further aspect of the invention there is thus provided a pharmaceutical formulation including any of the compounds of the invention, or pharmaceutically acceptable derivatives thereof, in admixture with pharmaceutically acceptable adjuvants, diluents and/or carriers.

Pharmacological Properties

The present compounds of formula (I) will be adapted for the prophylaxis and/or treatment of clinical conditions associated with reduced sensitivity to insulin (insulin resistance) and associated metabolic disorders. These clinical conditions will include, but will not be limited to, abdominal obesity, arterial hypertension, hyperinsulinaemia, hyperglycaemia, non insulin dependent diabetes mellitus (NIDDM) and the dyslipidaemia characteristically appearing with insulin resistance. This dyslipidaemia, also known as the atherogenic lipoprotein profile of phenotype B, is characterised by moderately elevated non-esterified fatty acids, elevated very low density lipoproteins (VLDL) triglycerides, low high density lipoproteins (HDL) cholesterol and the presence of small, dense, low density lipoproteins (LDL). Treatment with the present compounds is expected to lower the cardiovascular morbidity and mortality associated with atherosclerosis. These cardiovascular disease conditions include macro-angiophaties causing myocardial infarction, cerebrovascular disease and peripheral arterial insufficiency of the lower extremities. Because of their insulin sensitizing effect compounds of formula (1) are also expected to reduce the progress of clinical conditions associated with chronic hyperglycaemia in diabetes like the micro-angiophaties causing renal disease and retinal damage. Furthermore the compounds may be useful in treatment of various conditions outside the cardiovascular system associated with insulin resistance like the polycystic ovarian syndrome.

Working Examples $^1$H NMR and $^{13}$C NMR measurements were performed on a BRUKER ACP 300 or Varian UNITY plus 400, 500 or 600 spectrometers, operating at $^1$H frequencies of 300, 400, 500 and 600 MHz, respectively, and at $^{13}$C frequencies of 75, 100, 125 and 150 MHz, respectively.

Unless otherwise stated, chemical shifts are given in ppm with the solvent as internal standard.

Biological Activity

The biological activity of the compounds of the invention was tested in obese diabetic mice of the Umeå ob/ob strain. Groups of mice received the test compound by gavage once daily for 7 days. On the last day of the experiment the animals were anesthetized 2 h after dose in a non-fed state and blood was collected from an incised artery. Plasma was analyzed for concentration of glucose, insulin and triglycerides. A group of untreated obese diabetic mice of the same age served as control. The weight of the mice was measured before and after the experiment and the obtained weight gain was compared to the weight gain of the control animals. The individual values for glucose, insulin and triglyceride levels of the mice from the test group were expressed as the percent range of the corresponding values from the control group.

The desired "therapeutic effect" was calculated as the average percent reduction of the three variables glucose, insulin and triglycerides below the levels in the control animals. The therapeutic effect of the tested compounds according to the invention was compared to the same effect in the prior art compound troglitazone, administrered by gavage in the oral dose of 100 µmol/kg for 7 days.

The superior effects of the tested compounds according to the invention compared to that of troglitazone when given in the same oral dose demonstrate the increased potency and efficiacy of the claimed compounds.

| Abbreviations | |
|---|---|
| IRS | insulin resistance syndrom |
| VLDL | very low density lipoproteins |
| HDL | high density lipoproteins |
| LHMDS | lithium hexamethyldisilylamine |
| DMF | dimethylformamide |
| HOBtxH$_2$O | 1-hydroxybenzotriazole-hydrate |
| DMSO | dimethyl sulfoxide |
| DIBAL | diisobutylaluminium hydride |
| t | triplet |
| s | singlet |
| d | doublet |
| q | quartet |
| qvint | quintet |
| m | multiplet |
| br | broad |

EXAMPLE 1

3-{4-[(4-{[Anilino(methylimino)methyl] amino}phenethyl)oxy]phenyl}-2-ethoxypropanoic acid 3-{4-[(4-Aminophenethyl)oxy]phenyl}-2-ethoxypropanoic acid (20 mg, 0.061 mmol) and methyl N'-methyl-N-phenylcarbamimidothioate (11.5 mg, 0.064 mmol) were mixed in 0.3 ml DMF. Triethylamine (25.5 ml, 0.183 mmol) was added. The mixture was then cooled in an ice-bath and mercury (II)chloride (18 mg, 0.066 mmol) was added. After 30 minutes, the cooling bath was removed. The reaction mixture was stirred overnight. Water (1 ml) and ethyl acetate (0.5 ml) were added and then hydromatrix (ca. 0.5 g) was added. After a while, the mixture was filtered. The filtrate was evaporated to dryness. Chromatography of the residue on an ISOLUTE column (SI, 500 mg/3 ml) using ethyl acetate/heptane (10:90, then 25:75, and then 50:50) as eluant gave 5 mg, yield 18% of the desired product.

$^1$H NMR (400 MHz, CDCl$_3$): d 1.10 (t, J=7 Hz, 3H), 2.76 (dd, J=14, 7 Hz, 1H), 2.91 (dd, J=14, 5 Hz, 1H), 2.93 (d, J=5 Hz, 3H), 2.98 (t, J=7 Hz, 2H), 3.15–3.23 (m, 1H), 3.33–3.41 (m, 1H), 3.61 (s, br, 2H), 3.83 (dd, J=7, 5 Hz, 1H), 4.06–4.10 (m, 2H), 6.66 (d, J=8.4 Hz, 2H), 6.76 (d, J=8.8 Hz, 2H), 6.84 (d, J=8.8 Hz, 2H), 6.92 (s, br, 2H), 7.07 (d, J=8.8 Hz, 2H), and 7.39–7.43 (m, 3H).

EXAMPLE 2

3-{4-[(4-{[Anilino(phenylimino)methyl]amino}phenethyl)oxy]phenyl}-2-ethoxypropanoic acid 3-{4-[(4-Aminophenethyl)oxy]phenyl}-2-ethoxypropanoic acid (20 mg, 0.061 mmol) and methyl N,N'-diphenylcarbamimidothioate hydroiodide (23.7 mg, 0.064 mmol) were mixed in 0.3 ml N,N-dimethylformamide. Triethylamine (34 ml, 0.244 mmol) was added. The mixture was then cooled in an ice-bath. Mercury (II)chloride (18 mg, 0.066 mmol) was added. After 30 minutes, the cooling bath was removed. The reaction mixture was stirred overnight. Water (1 ml) and ethyl acetate (0.5 ml) were added and then hydromatrix (ca. 0.5 g) was added. After a while, the mixture was filtered. The filtrate was evaporated to dryness. Chromatography of the residue on an ISOLUTE column (SI, 500 mg/3 ml) using ethyl acetate/heptane (10:90, then 25:75, and then 50:50) as eluant gave 16 mg, yield 50% of the desired product.

$^1$H NMR (400 MHz, CDCl$_3$): d 1.20 (t, J=7 Hz, 3H), 2.95 (dd, J=15, 7 Hz, 1H), 2.98 (t, J=7 Hz, 2 H), 3.16 (dd, J=15, 4 Hz, 1H), 3.48–3.62 (m, 2H), 4.02–4.07 (m, 3H), 6.78 (d, J=8.8 Hz, 2H), 7.01–7.05 (m 1H), 7.14 (d, J=8.8 Hz, 4H), 7.20–7.36 (m, 9H), 7.48 (d, J=8.8 Hz, 2H) and 8.32 (s, 1H).

EXAMPLE 3

3-(4-{[4-({[(tert-Butoxycarbonyl)amino][(tert-butoxycarbonyl)imino]methyl}amino)phenethyl]oxy}phenyl)-2-ethoxypropanoic acid 3-{4-[(4-Aminophenethyl)oxy]phenyl}-2-ethoxypropanoic acid (20 mg, 0.061 mmol) and tert-butyl-[(tert-butoxycarbonyl)amino](methylsulfanyl)methylidenecarbamate (18.6 mg, 0.064 mmol) were mixed in 0.3 ml DMF. Triethylamine (25.5 ml, 0.183 mmol) was added. The mixture was then cooled in an ice-bath. Mercury (II)chloride (18 mg, 0.066 mmol) was added. After 30 minutes, the cooling bath was removed. The reaction mixture was stirred overnight. Water (1 ml) and ethyl acetate (0.5 ml) were added and then hydromatrix (ca. 0.5 g) was added. After a while, the mixture was filtered. The filtrate was evaporated to dryness. Chromatography of the residue on an ISOLUTE column (SI, 500 mg/3 ml) using ethyl acetate/heptane (10:90, then 25:75, and then 50:50) as eluant gave 15.4 mg, yield 44% of the desired product.

$^1$H NMR (400 MHz, CDCl$_3$): d 1.15 (t, J=7 Hz, 3H), 1.49 (s, 9H), 1.54 (s, 9H), 2.85 (dd, J=15, 8 Hz, 1H), 3.06 (t, J=7 Hz, 2H), 3.09 (dd, J=15, 4 Hz, 1H), 3.37–3.54 (m, 2H), 3.95 (dd, J=8, 4 Hz, 1H), 4.13 (t, J=7 Hz, 2H), 6.82 (d, J=8.4 Hz, 2H), 7.14 (d, J=8.4 Hz, 2H), 7.24 (d, J=8.4 Hz, 2H), 7.46 (d, J=8.4 Hz, 2H), 8.31 (s, 1H) and 9.87 (s, 1H).

EXAMPLE 4

3-(4-{[4-({[(tert-butoxycarbonyl)amino][(tert-butoxycarbonyl)imino]methyl}amino)phenethyl]oxy}phenyl)-2(S)-ethoxypropanoic acid 3-{4-[(4-Aminophenethyl)oxy]phenyl}-2(S)-ethoxypropanoic acid (223 mg, 0.61 mmol) and tert-butyl-[(tert-butoxycarbonyl)amino](methylsulfanyl)methylidenecarbamate (186 mg, 0.64 mmol) were mixed in 3 ml DMF. Triethylamine (0.34 ml, 2.44 mmol) was added. The mixture was then cooled in an ice-bath. Mercury (II)chloride (180 mg, 0.66 mmol) was added. After 30 minutes, the cooling bath was removed. The reaction mixture was stirred overnight. Water and ethyl acetate were added into the mixture. The organic phase was separated, dried with magnesium sulfate and the solvent was evaporated in vacuum. Column chromatography of the residue on silica gel using ethyl acetate/heptane (10:90, then 25:75) as eluant gave 135 mg, yield 39% of the desired product.

$^1$H NMR (500 MHz, CDCl$_3$): d 1.14 (t, J=7 Hz, 3H), 1.48 (s, 9H), 1.53 (s, 9H), 2.84 (dd, J=15, 8 Hz, 1H), 3.05 (t, J=7 Hz, 2H), 3.08 (dd, J=15, 4 Hz, 1H), 3.37–3.53 (m, 2H), 3.94 (dd, J=8,4 Hz, 1H), 4.12 (t, J=7 Hz, 2H), 6.82 (d, J=8.4 Hz, 2H), 7.14 (d, J=8.4 Hz, 2H), 7.23 (d, J=8.4 Hz, 2H), 7.46 (d, J=8.4 Hz, 2H) 8.33 (s, 1H) and 9.87 (s, 1H).

$^{13}$C NMR (125 MHz, CDCl$_3$): d 15.05, 27.90 (3C), 28.03 (3C), 35.17, 38.02, 66.99, 68.62, 81.68, 82.52, 83.30, 114.35 (2C), 120.17(2C), 128.83, 129.44 (2C), 130.50 (2C), 133.93, 135.75, 149.0, 150.66, 153.25, 157.62 and 171.16.

Starting Material (a) 3-{4-[2-(4-tert-Butoxycarbonylaminophenyl)ethoxy]phenyl}-(S)-2-ethoxypronanoic acid.

The enantiomers of 3-{4-[2-(4-tert-butoxycarbonylaminophenyl)ethoxy]phenyl}-2-ethoxypropanoic acid was separated with chiral preparative HPLC (Chiralpak AD 250×20 mm) using heptane, isopropanol and trifluoroacetic acid (80/20/0.5) as mobile phase giving 3-{4-[2-(4-tert-butoxycarbonylaminophenyl)ethoxy]phenyl }-(S)-2-ethoxypropanoic acid as a pure enantiomer.

$^1$H-NMR (600 MHz; CDCl$_3$): δ 1.17 (t, 3H), 1.51 (s, 9H), 2.93 (dd, 1H), 3.02 (t, 2H), 3.07 (dd, 1H), 3.42–3.47 (m, 1H), 3.55–3.6 (m, 1H), 4.04 (dd, 1H), 4.1 (t, 2H), 6.5 (bs, 1H), 6.8 (d, 2H), 7.13 (d, 2H), 7.19 (d, 2H), 7.28 (d, 2H).

$^{13}$C-NMR (100 MHz; CD$_3$OD): δ 15.3, 28.7, 36.1, 39.3, 67.1, 69.9, 80.7, 81.3, 115.4, 120.0, 130.3, 130.7, 131.4, 134.2, 138.8, 155.4, 159.1, 176.0.

(b) 3-{4-[2-(4-tert-Butoxycarbonylaminophenyl)ethoxy]phenyl}-2-ethoxypropanoic acid Lithium hydroxide hydrate (77 mg; 1.85 mmole) in water (5.5 ml) was slowly added to a solution of 3-{4-[2-(4-tert-butoxycarbonylaminophenyl)ethoxy]phenyl}-2-ethoxypropanoic acid ethyl ester (0.77 g; 1.68 mmole) in tetrahydrofuran (7.6 ml). After stirring at room temperature for 4 hours the reaction mixture was kept in a freezer for 4 days. Tetrahydrofuran was removed by evaporation in vacuo. More water was added and the mixture was acidified with hydrochloric acid to pH 1. The product was extracted with ethyl acetate, washed twice with water, dried (sodium sulfate), filtered and the solvent was evaporated in vacuo to give 0.716 g of 3-{4-[2-(4-tert-butoxycarbonylaminophenyl)-ethoxy]phenyl}-2-ethoxypropanoic acid.

$^1$H-NMR (400 MHz; CDCl$_3$): d 1.18 (t, 3H, J=7 Hz), 1.54 (s, 9H), 2.93–3.10 (m, 4H), 3.36–3.45 (m, 1H), 3.60–3.69 (m, 1H), 4.02–4.07 (m, 1H), 4.12 (t, 2H, J=7 Hz), 6.83 (dm, 2H, J=8.8 Hz, unresolved), 7.15–7.23 (m, 4H), 7.27–7.34 (m, 2H), 10.28 (bs, 1H).

$^{13}$C-NMR (100 MHz; CDCl$_3$): d 15.0, 28.3, 35.2, 38.0, 66.7, 68.8, 79.9, 80.7, 114.6, 119.1, 129.0, 129.4, 130.4, 133.1, 136.8, 153.2, 157.8, 175.3.

(c) 3-{4-[2-(4-tert-Butoxycarbonylaminophenyl)ethoxy]phenyl}-2-ethoxypropanoic acid ethyl ester 4-(2-Hydroxyethyl)phenylcarbamic acid tert-butyl ester (1.03 g; 4.34 mmole) and 2-ethoxy-3-(4-hydroxyphenyl)propanoic acid ethyl ester (1.03 g; 4.34 mmole) were dissolved in dichloromethane under argon at room temperature. Azodicarbonyl dipiperidine (1.65 g; 6.5 mmole) and thereafter triphenylphosphine (1.37 g; 5.2 mmole) were added. After stirring at room temperature for 6 hours the solvent was evaporated in vacuo. Purification by chromatography on silica gel using heptan:ethyl acetate (2:1) as eluant gave 1.78 g (yield 89%) of 3-{4-[2-(4-tert-butoxycarbonylaminophenyl)ethoxy]-phenyl}-2-ethoxypropanoic acid ethyl ester.

$^1$H-NMR (400 MHz; CDCl$_3$): d 1.17 (t, 3H, J=7 Hz), 1.23 (t, 3H, J=7 Hz), 1.53 (s, 9H), 2.94–2.97 (m, 2H), 3.03 (t, 2H, J=7.1 Hz), 3.31–3.40 (m, 1H), 3.56–3.65 (m, 1H), 3.95–4.0 (m, 1H), 4.11 (t, 2H, J=7.1 Hz), 4.17 (q, 2H, J=7 Hz), 6.60 (s, 1NH), 6.81 (dm, 2H, J=8.3 Hz, unresolved), 7.15 (dm, 2H, J=8.3 Hz, unresolved), 7.20 (dm, 2H, J=8.3 Hz, unresolved), 7.31 (dm, 2H, J=8.3 Hz, unresolved).

$^{13}$C-NMR (100 MHz; CDCl$_3$): d 14.1, 15.0, 28.3, 35.0, 38.4, 60.7, 66.1, 68.6, 80.26, 80.32, 114.3, 118.7, 128.2, 129.4, 130.3, 132.8, 136.7, 152.8, 157.5, 172.4.

(d) 4-(2-Hydroxyethyl)phenylcarbamic acid tert-butyl ester

Di-tert-Butyl dicarbonate (7.95 g; 36 mmole) was added to a mixture of p-aminophenethyl alcohol (5 g; 36 mmole) in tetrahydrofuran at 0° C. After stirring at room temperature over night, the solvent was evaporated in vacuo to give 8 g (yield 94%) of 4-(2-hydroxyethyl)phenylcarbamic acid tert-butyl ester.

$^1$H-NMR (400 MHz; DMSO-d$_6$): d 1,5 (s, 9H), 2,65 (dd, 2H), 3,55 (dd, 2H), 4,6 (bs, 1 OH), 7,1 (unresolved, 2H), 7,35 (unresolved, 2H), 9,1 (s, 1 NH).

$^{13}$C-NMR (100 MHz; DMSO-d$_6$): d 28.3, 38.6, 62.5, 78.9, 118.3, 129.1, 133.2, 136.6, 153.0.

(e) 2-Ethoxy-3-(4-hydroxyphenyl)propanoic acid ethyl ester 3-(4-Benzyloxyphenyl)-2-ethoxyacrylic acid ethyl ester (62 g; 0.19 mole) was hydrogenated in ethyl acetate (400 ml) at atmospheric pressure using Pd/C (10%) as catalyst. The mixture was filtered through celite and evaporated in vacuo to give 45.6 g (yield 100%) of 2-ethoxy-3-(4-hydroxyphenyl)propanoic acid ethyl ester.

$^1$H-NMR (600 MHz; CDCl$_3$): d 1.17 (t, 3H, J=7 Hz), 1.23 (t, 3H, J=7 Hz), 2.95 (d, 2H, J=6.6 Hz), 3.35–3.42 (m, 1H), 3.58–3.64 (m, 1H), 4.0 (t, 1H, J=6.6 Hz), 4.17 (q, 2H, J=7 Hz), 5.97 (s, 1 OH), 6.74 (dm, 2H, J=8.5 Hz, unresolved), 7.08 (dm, 2H, J=8.5 Hz, unresolved).

$^{13}$C-NMR (125 MHz; CDCl$_3$): d 14.0, 14.8, 38.3, 61.0, 66.1, 80.3, 115.1, 128.2, 130.3, 154.8, 173.0.

(f) 3-(4-Benzyloxyphenyl)-2-ethoxyacrylic acid ethyl ester

Tetramethylguanidine (33 g; 0.286 mole) was added to a solution of 4-benzyloxybenzaldehyde (59.1 g; 0.278 mole) and 101.8 g; 0.237 mole ) (1,2-diethoxy-2-oxyethyl) (triphenyl) phosphonium chloride in dichloromethane (600 ml) at 0° C. After stirring at room temperature over night, the solvent was evaporated in vacuo. The residue was dissolved in diethyl ether, insoluble material was filtered off and the filtrate was evaporated. The residue was stirred overnight with sodium bisulfite (saturated water solution) and diethyl ether. The solid material was filtered off. The filtrate was extracted with diethyl ether, dried (magnesium sulfate) and the solvent was evaporated in vacuo. Purification of the crude product by flash chromatography and crystallization in isopropanol gave 66.8 g (yield 86.3%) of 3-(4-benzyloxyphenyl)-2-ethoxyacrylic acid ethyl ester.

$^{13}$C-NMR (125 MHz; CDCl$_3$): d 14.4, 15.6, 61.0, 67.5, 70.0, 114.8, 124.0, 126.7, 127.5, 128.1, 128.6, 131.7, 136.7, 143.1, 159.2, 165.0.

EXAMPLE 5

(2S)-3-(4-{4-[4-({[(tert-butoxycarbonyl)amino][(tert-butoxycarbonyl)imino]methyl}amino)phenyl]butoxy}phenyl)-2-ethoxypropanoic acid (2S)-3-{4-[4-(4-Aminophenyl)butoxy]phenyl}-2-ethoxypropanoic acid (140 mg, 0.392 mmol) was dissolved in THF (10 ml). 1,3-Bis(tert-butoxycarbonyl)-2-methyl-2-thiopseudourea (116 mg, 0.392 mmol) was added and then N,N-diisopropylethylamine (126 mg, 0.979 mmol) was added. The mixture was stirred at room temperature for 12 days and thereafter evaporated in vacuum to dryness. Water and ethyl acetate were added into the residue. The mixture was then acidified with 1% hydrochloric acid, pH~3. The two phases were separated. The water phase was extracted with ethyl acetate (×2). All organic phases were combined and washed with brine and dried with magnesium sulfate. The solvent was evaporated. Chromatography of the residue on an ISOLUTE column (SI, 2 g/6 ml) using DCM and then MeOH/DCM (1:99) as eluant gave an oil. Re-chromatography of the oil on an ISOLUTE column (SI, 2 g/6 ml) using DCM and then MeOH/DCM (0.5:99.5) gave 88 mg desired product, yield 37.5%.

$^1$H NMR (500 MHz, CDCl$_3$): d 1.17 (t, J=7 Hz, 3H), 1.50 (s, 9H), 1.54 (s, 9H), 1.73–1.83 (m, 4H), 2.64 (t, J=7 Hz, 2H), 2.94 (dd, J=8, 14 Hz, 1H), 3.06 (dd, J=4, 14 Hz, 1H), 3.40–3.46 (m, 1H), 3.57–3.63 (m, 1H), 3.94 (t, J=6 Hz, 2H), 4.03 (dd, J=8, 4 Hz, 1H), 6.82 (d, J=8.5 Hz, 2H), 7.15 (d, J=7.5 Hz, 4H), 7.49 (d, J=8.5 Hz, 2H) and 10.27 (s, br, 1H).

$^{13}$C NMR (125 MHz, CDCl$_3$): d 15.01, 27.79, 28.13 (6C), 28.75, 34.96, 37.83, 66.75, 67.65, 79.53, 79.83, 83.58, 114 32 (2C), 122.32 (2C), 128.53, 128.76 (2C), 130.38 (2C), 134.45, 138.78, 153.29, 153.55, 157.95, 163.48 and 175.05.

Starting Material (a) (2S)-3-{4-[4-(4-Aminophenyl)butoxy]phenyl}-2-ethoxyprovanoic acid (2S)-2-Ethoxy-3-{4-[4-(4-nitrophenyl)butoxy]phenyl }propanoic acid (805 mg, 2.078 mmol) was dissolved in ethyl acetate (20 ml). A small amount of Pd/C (10%, with 56% moisture) was added. Hydrogenation was done at room temperature under atmospheric pressure and the reaction was followed by HPLC. After 2.5 hours, the reaction was complete. The mixture was filtered (celite). The filtrate was evaporated in vacuum. Chromatography of the residue on an ISOLUTE column (SI, 2 g/6 ml) using DCM, then MeOH/DCM (2:98) as eluant gave 655mg desired product, yield 88%.

$^1$H NMR (500 MHz, CD$_3$OD): d 1.11 (t, J=7 Hz, 31H), 1.70–1.76 (m, 4H), 2.56 (t, J=7 Hz, 2H), 2.83 (dd, J=14, 8 Hz, 1H), 2.95 (dd, J=14, 4 Hz, 1H), 3.30–3.35 (m, 1H), 3.55–3.61 (m, 1H), 3.92 (t, J=6 Hz, 2H), 3.96 (dd, J=8, 4 Hz, 1H), 6.73 (d, J=8 Hz, 2H), 6.78 (d, J=8.6 Hz, 2H), 6.99 (d, J=8 Hz, 2H) and 7.13 (d, J=8.6 Hz, 2H).

(b) (2S)-2-Ethoxy-3-{4-[4-(4-nitrophenyl)butoxy]phenyl}propanoic acid

Ethyl (2S)-2-ethoxy-3-{4-[4-(4-nitrophenyl)butoxy]phenyl}propanoate (1.05 g, 2.527 mmol) was dissolved in THF (20 ml). Under stirring, lithium hydroxide (78.7 mg, 3.285 mmol) in water (10 ml) was added in. The mixture was stirred at room temperature overnight. It was evaporated in vacuum to remove THF. The residue was extracted with diethyl ether. The obtained water phase was acidified with 10% hydrochloric acid, pH -3 and then extracted with ethyl acetate (×2). The organic phases were combined and washed with water and brine and dried with magnesium sulfate. The solvent was evaporated in vacuum. The desired product (926 mg) was obtained, yield 95%.

$^1$H NMR (400 MHz, CDCl$_3$): d 1.19 (t, J=7 Hz, 3H), 1.80–1.91 (m, 4H), 2.81 (t, J=7 Hz, 2H), 2.97 (dd, J=14, 7 Hz, 1H), 3.09 (dd, J=14, 4 Hz, 1H), 3.44–3.51 (m 1H), 3.58–3.66 (m, 1H), 3.98 (t, J=6 Hz, 2H), 4.07 (dd, J=7, 4 Hz, 1H), 6.83 (d, J=8.8 Hz, 2H), 7.17 (d, J=8.8 Hz, 2H), 7.36 (d, J=8.8 Hz, 2H) and 8.16 (d, J=8.8 Hz, 2H).

(c) Ethyl (2S)-2-ethoxy-3-{4-[4-(4-nitrophenyl)butoxy]phenyl}propanoate (S)-2-Ethoxy-3-(4-hydroxyphenyl)propanoic acid ethyl ester (1.0 g, 4.197 mmol) and 4-(4-nitrophenyl)butyl methanesulfonate (1.204 g, 4.406 mmol) were mixed in acetonitrile (20 ml). Potassium carbonate (anhydrous, 870 mg, 6.295 mmol) was added. The mixture was heated to reflux overnight. It was then evaporated in vacuum. Water and ethyl acetate were added into the residue. The two phases were separated. The organic phase was washed with water and brine and dried with magnesium sulfate. The solvent was removed by evaporation in vacuum. Column chromatography of the residue on silica gel using ethyl acetate/heptane (25:75) as eluant gave the desired product (1.62 g), yield 93%.

$^1$H NMR (400 MHz, CDCl$_3$): d 1.17 (t, J=7 Hz, 3H), 1.24 (t, J=7 Hz, 3H), 1.80–1.90 (m, 4H), 2.80 (t, J=7 Hz, 2H), 2.94–2.98 (m, 2H), 3.32–3.40 (m 1H), 3.57–3.65 (m 1H), 3.95–4.0 (m, 3H), 4.18 (q, J=7 Hz, 2H), 6.81 (d, J=8.8 Hz, 2H), 7.16 (d, J=8.8 Hz, 2H), 7.36 (d, J=8.8 Hz, 2H) and 8.15 (d, J=8.8 Hz, 2H)

(d) 4-(4-Nitrophenyl)butyl methanesulfonate 4-(4-Nitrophenyl)-1-Butanol (2.5 g, 12.166 mmol) was dissolved in DCM (50 ml). The solution was cooled in an ice-bath. Triethylamine (2.45 ml, 15.2 mmol) was added and then methanesulfonyl chloride (1.533 g, 13.382 mmol) was dropped in. After 1 hour, the ice-bath was removed. The mixture was stirred for 4 hours more. The reaction mixture was washed with water, sodium hydrogencarbonate aqueous solution (1%) and water (×3) and dried with magnesium sulfate. The solvent was evaporated in vacuum and the desired product (3.25 g) was obtained, yield 98%.

$^1$H NMR (400 MHz, CDCl$_3$): d 1.79–1.83 (m, 4H), 2.76–2.80 (m, 2H), 3.02 (s, 3H), 4.25–4.29(m, 2H), 7.35 (d, J=7 Hz, 2H) and 8.16 (d, with splits, 2H).

EXAMPLE 6

(2S)-3-(4-{3-[4-({[(tert-Butoxycarbonyl)amino][(tert-butoxycarbonyl)imino]methyl}amino)phenyl]propoxy}phenyl)-2-ethoxypropanoic acid 4-(3-{4-[(2S)-2-Carboxy-2-ethoxyethyl]phenoxy}propyl)benzenaminium chloride (152 mg, 0.4 mmol) was in isopropyl alcohol (3 ml). N,N-diisopropylethylamine (0.28 ml, 1.6 mmol) was added. The mixture was stirred for 5 minutes, then 1,3-bis(tert-butoxycarbonyl)-2-methyl-2-thiopseudourea (290 mg, 0.4 mmol) was added. The mixture was stirred at room temperature for 7 days and thereafter evaporated in vacuum to dryness. Water and ethyl acetate were added into the residue. The mixture was acidified with 1% hydrochloric acid, pH~5 and there was some precipitation. The two phase mixture was filtered and then separated. The pH of the water phase was further adjusted to ~3 and the water phase was extracted with ethyl acetate (×2). All organic phases were combined and washed with brine and dried with magnesium sulfate. The solvent was evaporated in vacuum. Chromatography of the residue on an ISOLUTE column (SI, 2 g/6 ml) using heptane/DCM (50:50), then DCM and MeOH/DCM (0.5: 99.5) as eluant gave the desired product (63 mg), yield 27%.

$^1$H NMR (400 MHz, CDCl$_3$): d 1.18 (t, J=7 Hz, 3H), 1.52 and 1.54 (s, s, separated at top, 18H), 2.04–2.11 (m, 2H), 2.78 (t, J=7 Hz, 2H), 2.95 (dd, J=14, 8 Hz, 1H), 3.07 (dd, J=14, 4 Hz, 1H), 3.40–3.48 (m, 1H), 3.57–3.65 (m, 1H), 3.94(t, 6.3 Hz, 2H), 4.04 (dd, J=8, 4 Hz, 1H), 6.83 (d, J=8.8 Hz, 2H), 7.16 (d, J=8.8 Hz, 2H), 7.17 (d, J=8.3 Hz, 2H), 7.50 (d, J=8.3 Hz, 2H) and 10.28 (br, 1H).

$^{13}$C NMR (100 MHz, CDCl$_3$): d 15.0, 28.09 (6C), 30.80, 31.55, 37.84, 66.73, 66.78, 79.53, 79.83, 83.59, 114.39 (2C), 122.37 (2C), 128.59, 128.86 (2C), 130.40 (2C), 134.62, 138.06, 153.28, 153.54, 157.91, 163.48 and 175.17.

Starting Material (a) 4-(3-{4-[(2S)-2-Carboxy-2-ethoxyethyl]phenoxy}propyl)benzenaminium chloride (2S)-3-[4-(3-{4-[(tert-Butoxycarbonyl)amino]phenyl}propoxy)phenyl]-2-ethoxypropanoic acid (301 mg, 0.679 mmol) was dissolved in ethyl acetate (15 ml) and the solution was cooled in an ice-bath. Ethyl acetate (cooled in an ice-bath, 55 ml) that was bubbled with hydrogen chloride (gas) for 10 minutes was dropped in. After the addition, the mixture was stirred for 1 hour. HPLC showed that the reaction was complete and there was some precipitation. The mixture was then concentrated in vacuum and more precipitation occurred. The white solid was collected by filtration. It was then washed with diethyl ether (×2) and dried in vacuum and 230 mg desired product was obtained, yield 89%.

$^1$H NMR (500 MHz, DMSO-d$_6$): d 1.02 (t, J=7 Hz, 3H), 1.95–2.01 (m, 2H), 2.73 (t, J=7.5 Hz, 2H), 2.78 (dd, J=14, 8 Hz, 1H), 2.87 (dd, J=14, 5 Hz, 1H), 3.26–3.32 (m, 1H), 3.47–3.53 (m, 1H), 3.86–3.94 (m, 3H), 6.81 (d, J=8.6 Hz, 2H), 7.11 (d, J=8.6 Hz, 2H), 7.20 (br, 2H), 7.31 (d, J=8 Hz, 2H) and 9.77 (br, 3H).

(b) (2S)-3-[4-(3-{4-[(tert-Butoxycarbonyl)amino]phenyl}propoxy)phenyl]-2-ethoxypropanoic acid Ethyl (2S)-3-[4-(3-{4-[(tert-butoxycarbonyl)amino]phenyl}propoxy)phenyl]-2-ethoxypropanoate (350 mg, 0.742 mmol) was dissolved in THF (10 ml). Under stirring, lithium hydroxide in water (5 ml) was added. The mixture was stirred at room temperature and followed by HPLC. After 4 hours, the reaction was stopped. More lithium hydroxide (9 mg) was added. The mixture was stirred overnight. It was then evaporated in vacuum to remove THF. The residue was extracted with diethyl ether and then acidified with 10% hydrochloric acid, pH~3, and extracted with ethyl acetate (×2). The organic phases were combined and washed with brine and dried with magnesium sulfate. The solvent was evaporated and white solid product (315 mg) was left, yield 96%.

¹H NMR (400 MHz, CDCl₃): d 1.19 (t, J=7 Hz, 3H), 1.54 (s, 9H), 2.03–2.10 (m, 2H), 2.76 (t, J=7 Hz, 2H), 2.97 (dd, J=14, 8 Hz, 1H), 3.07 (dd, J=14, 4 Hz, 1H), 3.39–3.46 (m, 1H), 3.61–3.68 (m, 1H), 3.93 (t, 6.3 Hz, 2H), 4.05 (dd, J=8, 4 Hz, 1H), 6.83 (d, J=8.8 Hz, 2H), 7.13 (d, J=8.8 Hz, 2H), 7.18 (d, J=8.8 Hz, 2H) and 7.26 (br, 2H).

(c) Ethyl (2S)-3-[4-(3-{4-[(tert-butoxycarbonyl)amino]phenyl}propoxy)phenyl]-2-ethoxypropanoate 3-{4-[(tert-Butoxycarbonyl)amino]phenyl}propyl methanesulfonate (360 mg, 1.093 mmol) and (S)-2-Ethoxy-3-(4-hydroxyphenyl)propanoic acid ethyl ester (260 mg, 1.093 mmol) were mixed in acetonitrile (30 ml). Potassium carbonate (anhydrous, 226.6 mg 1.639 mmol) was added. The mixture was heated to reflux overnight and thereafter it was evaporated to dry. Ethyl acetate (20 ml) and water (5 ml) were added into the residue. The two phases were separated and the water phase was extracted with ethyl acetate (10 ml×2). The organic phases were combined and washed with 0.1 M sodium hydroxide aqueous solution, water and brine and dried with magnesium sulfate. The solvent was evaporated in vacuum and an oil mixture was left. Column chromatography of the oil mixture on silica gel using ethyl acetate/heptane (20:80) as eluant gave the desired product (389 mg), yield 75.5%.

¹H NMR (400 MHz, CDCl₃): d 1.18 (t, J=7 Hz, 3H), 1.24 (t, J=7 Hz, 3H), 1.53 (s, 9H), 2.03–2.10 (m, 2H), 2.76 (t, J=7 Hz, 2H), 2.96 (d, J=6.3 Hz, 2H), 3.33–3.41 (m, 1H), 3.58–3.65 (m, 1H), 3.93 (t, 6.3 Hz, 2H), 3.99 (t, J=6.3 Hz, 1H), 4.18 (q, J=7 Hz, 2H), 6.46 (s, br, 1H), 6.81 (d, J=8 Hz, 2H), 7.13 (d, J=8 Hz, 2H), 7.15 (d, J=8 Hz, 2H) and 7.27 (d, with splits, J=8 Hz, 2H).

(d) 3-{4-[(tert-Butoxycarbonyl)amino]phenyl}propyl methanesulfonate tert-Butyl 4-(3-hydroxypropyl)phenylcarbamate (327 mg, 1.301 mmol) in DCM (15 ml) was cooled in an ice-bath. Triethylamine (0.23 ml, 1.626 mmol) was added, and then methanesulfonyl chloride (164 mg, 1.431 mmol) was added. The mixture was stirred overnight and the temperature was allowed going up to room temperature. It was then washed with water, sodium hydrogencarbonate aqueous solution (1%), water and brine and dried with magnesium sulfate. Evaporation in vacuum to remove the solvent gave the desired product (394 mg), yield 92%.

¹H NMR (400 MHz, CDCl₃): d 1.53 (s, 9H), 2.02–2.09 (m, 2H), 2.71(t, J=7 Hz, 2H), 3.00 (s, 3H), 4.22 (t, J=6.4 Hz, 2H), 6.43 (s, br, 1H), 7.12 (d, J=8.4 Hz, 2H) and 7.30 (d, J=8,4 Hz, 2H).

(e) tert-Butyl 4-(3-hydroxypropyl)phenylcarbamate

3-{4-[(tert-Butoxycarbonyl)amino]phenyl}propanoic acid (1.33 g, 5.013 mmol) and BOP reagent (2.882 g, 6.517 mmol) were mixed in THF (30 ml). DIPEA (907 mg, 7.018 mmol) was added. The mixture was stirred for 10 minutes. Sodium borohydride (246 mg, 6.517 mmol) was added. The mixture was stirred for 30 minutes more and then evaporated to dryness. Ethyl acetate and water were added into the residue. The organic phase was washed with water and brine and dried with magnesium sulfate. The solvent was evaporated and an oil mixture was obtained. Column chromatography of the oil on silica gel using ethyl acetate/heptane (10:90, then 25:75) as eluant gave the desired oil product (616 mg), yield 49%.

¹H NMR (500 MHz, CDCl₃): d 1.53 (s, 9H), 1.84–1.90 (m, 2H), 2.66 (t, J=6.7 Hz, 2H), 3.66 (t, J=6.4 Hz, 2H), 6.61 (s, br, 1H), 7.12 (d, J=8 Hz, 2H) and 7.28 (d, with splits, 2H).

(f) 3-{4-[(tert-Butoxycarbonyl)amino]phenyl}propanoic acid

Aminohydrocinnamic acid (1.652 g, 10.0 mmol) in THF (50 ml) was cooled in an ice-bath. Di-t-butyldicarbonate (2.183 g, 10.0 mmol) was added. The mixture was stirred over weekend and the temperature was allowed up to room temperature. HPLC showed that the reaction was not complete. 100 mg more of di-t-butyldicarbonate was added. The mixture was stirred for 3 hours more and evaporated in vacuum to dry. The residue was dissolved in DCM and washed with water and brine and dried with magnesium sulfate. Evaporation of the solvent gave the desired solid product (2.632g), yield 99%.

¹H NMR (400 MHz, CD₃OD): d 1.50 (s, 9H), 2.55 (t, J=7.8 Hz, 3H), 2.84 (t, J=7.8 Hz, 2H), 7.11 (d, J=8.5 Hz, 2H) and 7.28 (d, J=8.5 Hz, 2H).

The invention claimed is:
1. A compound of formula (I)

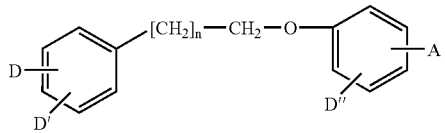

and stereo and optical isomers and racemates thereof as well as pharmaceutically acceptable salts, solvates, prodrugs, tautomers, and crystalline forms thereof, in which formula A is situated in the ortho, meta or para position and represents

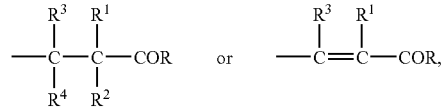

wherein
  R is hydrogen;
    —$OR^a$, wherein $R^a$ represents hydrogen, alkyl, aryl or alkylaryl;
    —$NR^aR^b$, wherein $R^a$ and $R^b$ are the same or different and $R^a$ is as defined above and $R^b$ represents hydrogen, alkyl, aryl, alkylaryl, cyano, —OH, —Oalkyl, —Oaryl, —Oalkylaryl, —$COR^c$ or —$SO_2R^d$, wherein $R^c$ represents hydrogen, alkyl, aryl or alkylaryl and $R^d$ represents alkyl, aryl or alkylaryl;
  $R^1$ is alkyl, aryl, alkene, alkyne, cyano;
    —$OR^e$, wherein $R^e$ is alkyl, acyl, aryl or alkylaryl;
    —O—$[CH_2]_m$—$OR^f$, wherein $R^f$ represents hydrogen, alkyl, acyl, aryl or alkylaryl and m represents an integer 1–8;
    —$OCONR^aR^c$, wherein $R^a$ and $R^c$ are as defined above;
    —$SR^d$, wherein $R^d$ is as defined above;
    —$SO_2NR^aR^f$, wherein $R^f$ and $R^a$ are as defined above;
    —$SO_2OR^d$, wherein $R^d$ is as defined above;
    —$COOR^d$, wherein $R^d$ is as defined above;
  $R^2$ is hydrogen, halogen, alkyl, aryl, or alkylaryl,
  $R^3$ and $R^4$ are the same or different and each represents hydrogen, alkyl, aryl, or alkylaryl,
  n is an integer 1–6,
  D is situated in the ortho, meta or para position and represents

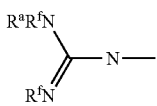

wherein R$^a$ and R$^f$ are as defined above;
D' is situated in the ortho, meta or para position and represents hydrogen, alkyl, acyl, aryl, alkylaryl, halogen, —CN, —NO$_2$, —NR$^f$R$^b$, wherein R$^f$ and R$^b$ are as defined above; —OR$^f$, wherein R$^f$ is as defined above; —OSO$_2$R$^d$, wherein R$^d$ is as defined above;
D" is situated in the ortho, meta or para position and represents hydrogen, alkyl, acyl, aryl, alkylaryl, halogen, —CN, —NO$_2$, —NR$^f$R$^b$ wherein R$^f$ and R$^b$ are as defined above; —OR$^f$, wherein R$^f$ is as defined above; —OSO$_2$R$^d$, wherein R$^d$ is as defined above.

2. A compound of claim 1 wherein A is situated in the meta or para position and represents,

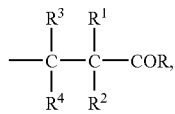

wherein
R is hydrogen;
—OR$^a$;
—NR$^a$R$^b$, wherein R$^b$ represents hydrogen, alkyl, aryl, alkylaryl, cyano, —OH, —Oalkyl or —Oalkylaryl;
R$^1$ is cyano; —OR$^d$;
—O—[CH2]$_m$—OR$^a$;
R$^2$ is hydrogen or alkyl;
R$^3$ is hydrogen or alkyl;
R$^4$ is hydrogen;
n is an integer 2–4;
D' is situated in the ortho, meta or para position and represents hydrogen, alkyl, alkylaryl, halogen, —CN or —NO$_2$; —OR$^h$ wherein R$^h$ is hydrogen or alkyl;
D" is situated in the ortho, meta or para position and represents hydrogen, alkyl, alkylaryl, halogen, —CN or —NO$_2$; —OR$^h$ wherein R$^h$ is hydrogen or alkyl.

3. A compound of claim 2, wherein
A is situated in the meta or para position;
R is —OR$^a$, wherein R$^a$ is hydrogen, alkyl or alkylaryl; —NHR$^b$, wherein R$^b$ is hydrogen, alkyl, alkylaryl, cyano, —Oalkyl or —Oalkylaryl;
R$^1$ is —Oalkyl;
R$^2$ is hydrogen or alkyl;
R$^3$ is hydrogen or alkyl;
R$^4$ is hydrogen;
n is an integer 2–4,
D is situated in the para position
D' is hydrogen, and
D" is hydrogen.

4. A compound of claim 3, wherein
A is situated in the para position;
R is —OH, —Oalkyl or —Oalkylaryl;
—NH$_2$, —NHOalkylaryl or —NHCN;
R$^1$ is —Oalkyl;
R$^2$ is hydrogen;
R$^3$ is hydrogen;
n is the integer 2 to 3;
D is situated in the para position,
and R$^f$ represents hydrogen, alkyl or —OCOR$^d$, wherein R$^d$ as defined in claim 1.

5. A compound of claim 4, wherein
D represents

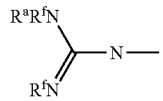

wherein R$^a$ is alkyl or aryl and R$^f$ is as defined in claim 4.

6. A compound of claim 5, wherein R is —OH, —Oalkyl or —Oalkylaryl.

7. A compound of claim 6, wherein D represents

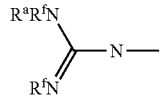

wherein R$^a$ is as defined in claim 6 and R$^f$ represents hydrogen, alkyl or —OCOR$^d$, wherein R$^d$ represents alkyl or aryl.

8. A compound according to claim 1 selected from:
3-{4-[(4-{[anilino(methylimino)methyl]amino}phenethyl)oxy]phenyl}-2-ethoxypropanoic acid;
3-{4-[(4-{[anilino(phenylimino)methyl]amino}phenethyl)oxy]phenyl}-2-ethoxypropanoic acid;
3-(4-{[4-({[(tert-butoxycarbonyl)amino][(tert-butoxycarbonyl)imino]methyl}amino)-phenethyl]oxy}phenyl)-2-ethoxypropanoic acid;
3-(4-{[4-({[(tert-butoxycarbonyl)amino][(tert-butoxycarbonyl)imino]methyl}amino)-phenethyl]oxy}phenyl)-2 (S)-ethoxypropanoic acid;
(2S)-3-(4-{4-[4-({[(tert-butoxycarbonyl)amino][(tert-butoxycarbonyl)imino]methyl}-amino)phenyl]butoxy}phenyl)-2-ethoxypropanoic acid; or
(2S)-3-(4-{3-[4-({[(tert-Butoxycarbonyl)amino][(tert-butoxycarbonyl)imino]methyl}amino)phenyl]propoxy}phenyl)-2-ethoxypropanoic acid; and pharmaceutically acceptable salts thereof.

9. A compound of any one of claims 1 to 6 or 7 for use as a medicament.

10. A pharmaceutical formulation comprising a compound of any one of claims 1 to 6, 7, or 8 and a pharmaceutically acceptable adjuvant, diluent or carrier.

11. A method for the treatment or prophylaxis of conditions associated with a patient having reduced sensitivity to insulin comprising administering to a patient a compound of any one of claims 1 to 6, 7, or 8.

* * * * *

UNITED STATES PATENT AND TRADEMARK OFFICE
CERTIFICATE OF CORRECTION

PATENT NO. : 7,169,810 B2 Page 1 of 1
APPLICATION NO. : 10/475054
DATED : October 17, 2003
INVENTOR(S) : Krister Bamberg et al.

It is certified that error appears in the above-identified patent and that said Letters Patent is hereby corrected as shown below:

Between Columns 25 and 26, Claim 1, between Lines 1-6, the chemical structure depicted "-N-" instead of "-NH-" and should read as follows:

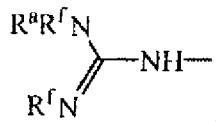

Between Columns 25 and 26, Claim 5, between Lines 11-15, the chemical structure depicted "-N-" instead of "-NH-" and should read as follows:

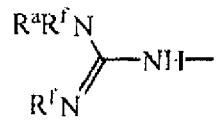

Between Columns 25 and 26, Claim 7, between Lines 21-28, the chemical structure depicted "-N-" instead of "-NH-" and should read as follows:

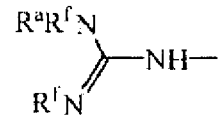

Signed and Sealed this

Sixteenth Day of June, 2009

JOHN DOLL
*Acting Director of the United States Patent and Trademark Office*

UNITED STATES PATENT AND TRADEMARK OFFICE
CERTIFICATE OF CORRECTION

PATENT NO. : 7,169,810 B2  Page 1 of 1
APPLICATION NO. : 10/475054
DATED : January 30, 2007
INVENTOR(S) : Krister Bamberg et al.

It is certified that error appears in the above-identified patent and that said Letters Patent is hereby corrected as shown below:

Between Columns 25 and 26, Claim 1, between Lines 1-6, the chemical structure depicted "-N-" instead of "-NH-" and should read as follows:

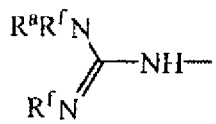

Between Columns 25 and 26, Claim 5, between Lines 11-15, the chemical structure depicted "-N-" instead of "-NH-" and should read as follows:

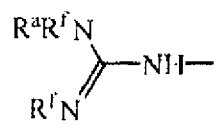

Between Columns 25 and 26, Claim 7, between Lines 21-28, the chemical structure depicted "-N-" instead of "-NH-" and should read as follows:

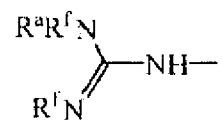

This certificate supersedes the Certificate of Correction issued June 16, 2009.

Signed and Sealed this

Fourteenth Day of July, 2009

JOHN DOLL
*Acting Director of the United States Patent and Trademark Office*